(12) United States Patent
Chen et al.

(10) Patent No.: US 7,253,617 B1
(45) Date of Patent: Aug. 7, 2007

(54) METHOD AND APPARATUS FOR CHARACTERIZING HEAVY OIL COMPONENTS IN PETROLEUM RESERVOIRS

(75) Inventors: Songhua Chen, Katy, TX (US); Sheng Fang, Houston, TX (US); Mike Gillen, The Woodlands, TX (US); Mette Stengaard Munkholm, Vanloese (DK); Wei Shao, Conroe, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 11/376,046

(22) Filed: Mar. 15, 2006

(51) Int. Cl.
*G01V 3/00* (2006.01)

(52) U.S. Cl. ............................... 324/303; 324/300

(58) Field of Classification Search ........ 324/300–324; 600/410–422
See application file for complete search history.

(56) References Cited

U.S. PATENT DOCUMENTS

| | | | |
|---|---|---|---|
| 4,338,567 A | * | 7/1982 | Coates ...................... 324/338 |
| 6,097,184 A | * | 8/2000 | Flaum ....................... 324/303 |
| 6,247,542 B1 | * | 6/2001 | Kruspe et al. ................ 175/40 |
| 6,346,813 B1 | * | 2/2002 | Kleinberg ................... 324/303 |
| 6,755,246 B2 | * | 6/2004 | Chen et al. ............ 166/250.01 |
| 6,891,369 B2 | * | 5/2005 | Hurlimann et al. ......... 324/303 |
| 6,941,804 B2 | * | 9/2005 | Hasem et al. ............. 73/152.24 |
| 7,075,297 B2 | * | 7/2006 | Freedman ................... 324/303 |
| 7,116,103 B2 | * | 10/2006 | Edwards et al. ............ 324/303 |
| 2002/0120429 A1 | | 8/2002 | Ortoleva |
| 2006/0154306 A1 | | 7/2006 | Kotlar et al. |

* cited by examiner

*Primary Examiner*—Brij B. Shrivastav
(74) *Attorney, Agent, or Firm*—Cantor Colburn LLP

(57) ABSTRACT

A method for obtaining a parameter of interest relating to a region investigated by a nuclear magnetic resonance (NMR) tool and a non-NMR tool is disclosed. Data arising from the NMR tool is acquired, and data arising from the non-NMR tool is acquired. A solution equation is utilized for NMR signal intensity, the solution equation being functionally related to the NMR data, and a solution constraint is utilized based at least partially on the non-NMR data. The solution equation is solved for the signal intensity subject to the solution constraint, wherein the solving provides information relating to the parameter of interest.

19 Claims, 4 Drawing Sheets

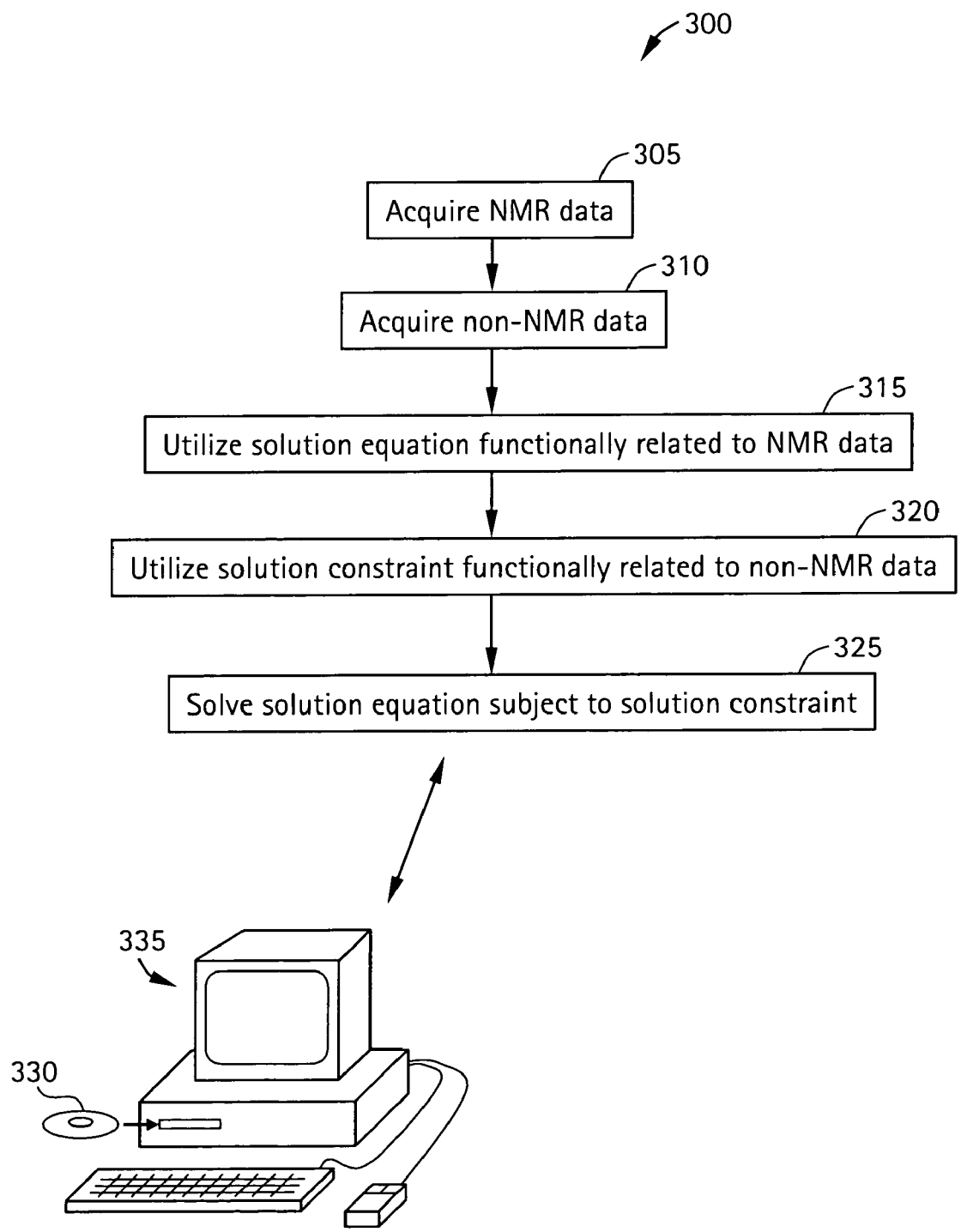

METHOD AND APPARATUS FOR CHARACTERIZING HEAVY OIL COMPONENTS IN PETROLEUM RESERVOIRS

BACKGROUND OF THE INVENTION

The present disclosure relates generally to the field of petroleum reservoir formation and fluid identification, more particularly to a method of determining heavy oil volume, and even more particularly to a method of distinguishing movable and non-movable portions of heavy oil components from wireline logging.

The ability to detect and quantify very viscous or heavy oil in petroleum reservoirs becomes more and more important as the discovery of conventional oils becomes more and more difficult while the worldwide consumption of petroleum products increases. Therefore, exploration and production of petroleum from heavy oil fields are inevitable trends as there are more proven heavy and very viscous oils reserves in the world than that of conventional oils.

Nuclear magnetic resonance (NMR) is one of the logging techniques that is useful for underground formation evaluation and fluid identification. In principle, the capability of identifying and quantifying fluid phases in porous media by NMR techniques is based on the sensitivity of NMR measured quantities, such as signal amplitude, diffusivity, relaxation times, and some combination thereof. NMR signature for heavy oil is characterized by very low diffusivity and short relaxation time, and, in extremely heavy oil reservoirs such as tar, the relaxation time can be so short that the signal is substantially decayed even before an NMR logging tool can detect it. Because the apparent relaxation time for both heavy oil and bound water (such as clay-bound-water, for example) are dominated by intrinsic relaxation mechanism (defined as the combination of bulk and surface relaxation rates), there is a great uncertainty in distinguishing heavy oil and bound water using relaxation time methods, diffusion contrast-based methods, or a combination of both methods.

The bound water in formation rock generally consists of clay-bound-water (CBW) and capillary bound (or irreducible) water (BVI). Often these two types of bound water volumes do not have a sharp boundary to separate them on a $T_2$ (transverse relaxation time) distribution, but it is generally true that CBW resides in smaller $T_2$ than BVI on a $T_2$ spectrum. When the formation contains heavy oil, CBW is less likely to be discernable from the heavy oil. On the other hand, there are other logging techniques that may be used to estimate the volume of CBW. For instance, the reading of GR (gamma ray) from GR logging, expressed in API (American Petroleum Institute), is often used as a CBW indicator.

NMR relaxation time for a single-component oil, such as hexane, exhibits a single or nearly-single exponential decay behavior. Crude oils contain many constituents having different carbon numbers and different molecular structures. Therefore the relaxation time for crude oil exhibits a broader distribution, and the distribution pattern often associates with the underlying crude oil constituents. The feature of constituent mixture in crude oil is not often characterized by downhole fluid-analyzing devices or by openhole logging. A single value of viscosity or specific gravity is usually inadequate to fully describe a system that is intrinsically multiple components in constituents.

The distribution of $T_2$ is potentially useful for characterizing the crude oil constituents. So far, however, NMR applications for fluid identification usually took a different route. Instead of utilizing the rich information provided by an oil $T_2$ spectrum, common practice is to reduce the distribution to a single value, often a geometric-mean $T_2$. Then this single value is correlated to the oil viscosity. However, the correlation is a less reliable quantity for heavy oil characterization, especially for extra-heavy oils. Additionally, this approach has failed to utilize $T_2$ distribution for providing the need information of fluid component analysis.

Viscosity is often a very useful parameter to describe a conventional crude oil because it is related to the flow properties that are essential to oil production. However, viscosity alone cannot fully describe a heavy oil flow property because heavy oil may contain more complicated molecules, such as asphaltenes, which may affect fluid flow in different manners, such as precipitation. Thus, the amount of asphaltene in crude oil affects the production and transportation of heavy oil from formation to wellhead to surface. If one can characterize the amount of asphaltenes in the logging stage, one can choose the optimal production method that minimizes the asphlatene deposition, thereby minimizing the formation damage and pipeline clogging.

Another method for identifying heavy oil involves actively or passively heating the formation and the fluids therein, then performing logging measurements at a temperature equilibrium state and at an artificially elevated state. Because $T_2$ of heavy oil is significantly affected by temperature, while $T_2$ of water in rock formations is much less affected by temperature, by determining whether there is a significant $T_2$ upshift as temperature increases one would be able to detect the presence of heavy oil in the formation that is otherwise indistinguishable by a single-temperature-state measurement alone.

The name heavy oil comes from the fact that the density of the oil is high. In the refinery industry, heavy oil is defined as the fuel oil remaining after the lighter oils have been distilled off during the refining process. For reservoir engineering, heavy oil is a type of crude petroleum characterized by high viscosity and a high carbon-to-hydrogen ratio. It is usually difficult and costly to produce by conventional techniques. The exact viscosity range for heavy oils varies.

Conventional crude oil may be viewed as oil that flows naturally or that can be pumped without being heated or diluted. Crude oil is commonly classified as light, medium, heavy or extra heavy, referring to its gravity as measured on the American Petroleum Institute (API) Scale, which is measured in degrees. U.S. industry defines light crude oil as having an API gravity higher than 31.1°, medium oil as having an API gravity between 31.1° and 22.3°, heavy oil as having an API gravity between 22.3° and 10°, and extra heavy oil (such as bitumen, for example) as having an API gravity of less than 10°. Canada has only two classifications, light oil with an API gravity greater than 25.7° API, and heavy oil with an API gravity less than 25.7° API. In other locations, such as the Lloydminster area of Alberta and Saskatchewan in Canada, heavy oil has API gravities ranging from 9° to 18°, and from the oilsands deposits in the Athabasca area of Alberta, Canada, heavy oil in the form of bitumen has an API gravity of around 8°. From the foregoing, it will be appreciated that the definition of heavy oil depends on the location of the deposits, having API gravities of 22.3° to 10° API for U.S. heavy oil, less than 10° for U.S. extra heavy oil, 18° to 9° for Alberta heavy oil, and 8° for Athabasca oilsands heavy oil, for example.

Accordingly, and from a practical standpoint, it would be more useful to define heavy and extra heavy oil in less rigorous terms. For practical purposes, it would be useful to relate heavy and extra-heavy oil based on the ability of the crude oil or oil components to flow, rather than the API values, because the API value is defined at a standard temperature and pressure condition of 1 atm and 60 degree-C., while the heavy oil reservoirs may be at different conditions. Thus, the viscosity values and the recoverability of the oil at a reservoir head may be substantially different from the standard condition. As such, and as herein used, the terms heavy oil and extra-heavy oil are referred to in relation to NMR characteristics, with heavy oil being defined as a viscous oil that has an intrinsic relaxation time upper-limit of approximately 5° ms (milliseconds) at reservoir condition, and extra heavy oil as more viscous oil that has an intrinsic relaxation time upper-limit of approximately 10 ms. Because crude oil contains hydrocarbons having a distribution of carbon-to-hydrogen ratio and chemical structures, a distribution of relaxation time is observed. The faster relaxing components are generally related to more viscous components and are less-likely to be producible with conventional oil recovery methods. It should also be noted, however, that the recoverability is also affected by the reservoir pressure. Thus, and as a practical matter, it is preferable not to define a clear-cut dividing line between heavy and extra heavy oils.

While existing petroleum reservoir analysis methods may be suitable for their intended purpose, there remains, however, a need in the art for an improved analytical method of determining heavy oil volume, and of distinguishing movable and non-movable portions of heavy oil components within a petroleum reservoir.

BRIEF DESCRIPTION OF THE INVENTION

An embodiment of the invention includes a method for obtaining a parameter of interest relating to a region investigated by a nuclear magnetic resonance (NMR) tool and a non-NMR tool. Data arising from the NMR tool is acquired, and data arising from the non-NMR tool is acquired. A solution equation is utilized for NMR signal intensity, the solution equation being functionally related to the NMR data, and a solution constraint is utilized based at least partially on the non-NMR data. The solution equation is solved for the signal intensity subject to the solution constraint, wherein the solving provides information relating to the parameter of interest.

Another embodiment of the invention includes a computer program product comprising a computer readable medium having computer readable program code on or embodied in the medium, the computer readable program code capable of implementing the aforementioned method.

BRIEF DESCRIPTION OF THE DRAWINGS

Referring to the exemplary drawings wherein like elements are numbered alike in the accompanying Figures:

FIG. 4 illustrates a method for obtaining a parameter of interest relating to a region investigated by a NMR tool and a non-NMR tool in accordance with an embodiment of the invention.

DETAILED DESCRIPTION OF THE INVENTION

In an embodiment of the invention, an analytical method determines separately the movable and extra-viscous components of heavy crude oils, which may be used to assess the producible volume and the likelihood of occurrence of asphaltene-precipitation caused formation clogging. NMR logging is used to determine heavy oil volume, and non-NMR logging is used to provide additional CBW information.

Figure 1:
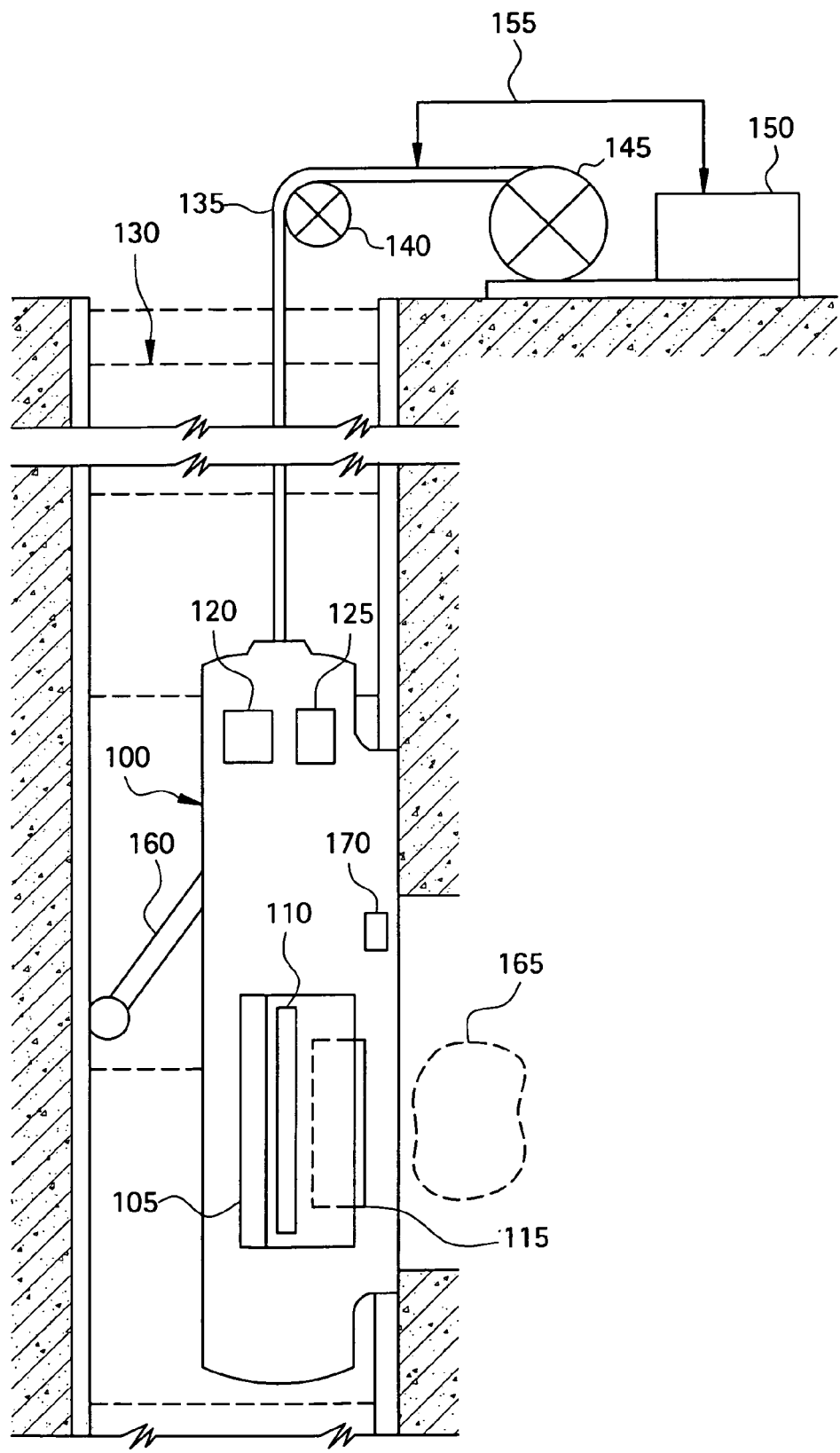
FIG. 1 is an exemplary embodiment of a nuclear magnetic resonance (NMR) well logging apparatus for use in accordance with an embodiment of the invention.

FIG. 1 is an exemplary embodiment of a nuclear magnetic resonance (NMR) well logging apparatus 100 suitable for detecting and quantifying a parameter of interest (discussed in more detail below) in a subterranean region. In an exemplary embodiment, apparatus 100 includes a magnetic field and field gradient generator 105, such as a permanent magnet for example, a RF signal generator 110, a resonance circuit and receiver 115, a processing circuit 120, and a storage medium 125. In an exemplary application, logging apparatus 100 is suspended in a borehole 130 via a cable 135, a pulley 140, a drivewheel 145, and surface equipment 150, which controls the lowering and raising action of cable 135 as represented by control line 155. Apparatus 100 may be pressed against one side of borehole 130 via a control arm 160. Field gradient generator 105 is capable of applying a static magnetic field gradient G to the subterranean region, generally represented at 165. Signal generator 110 is capable of applying a sequence of magnetic pulses to region 165, and signal receiver 115 is capable of receiving information, and specifically nuclear magnetic resonance information, from the nuclei of region 165 in response to the magnetic field gradient from field gradient generator 105 and the magnetic pulses from signal generator 110. The nuclei of the region, being subjected to a pulsed NMR technique, are productive of NMR echo data, and characteristically have a longitudinal relaxation time $T_1$ distribution and an apparent transverse relaxation time $T_{2app}$ distribution. In an embodiment, the pulses from signal generator 110 and the information received at signal receiver 115 are controlled and processed by processing circuit 120. Apparatus 100 may also include a non-NMR data gathering device 170, such as a gamma ray detector, which will be discussed in more detail below. Storage medium 125, readable by processing circuit 120, stores instructions for execution by processing circuit 120 for performing method embodiments of the invention, which will now be discussed in more detail.

Figure 2:
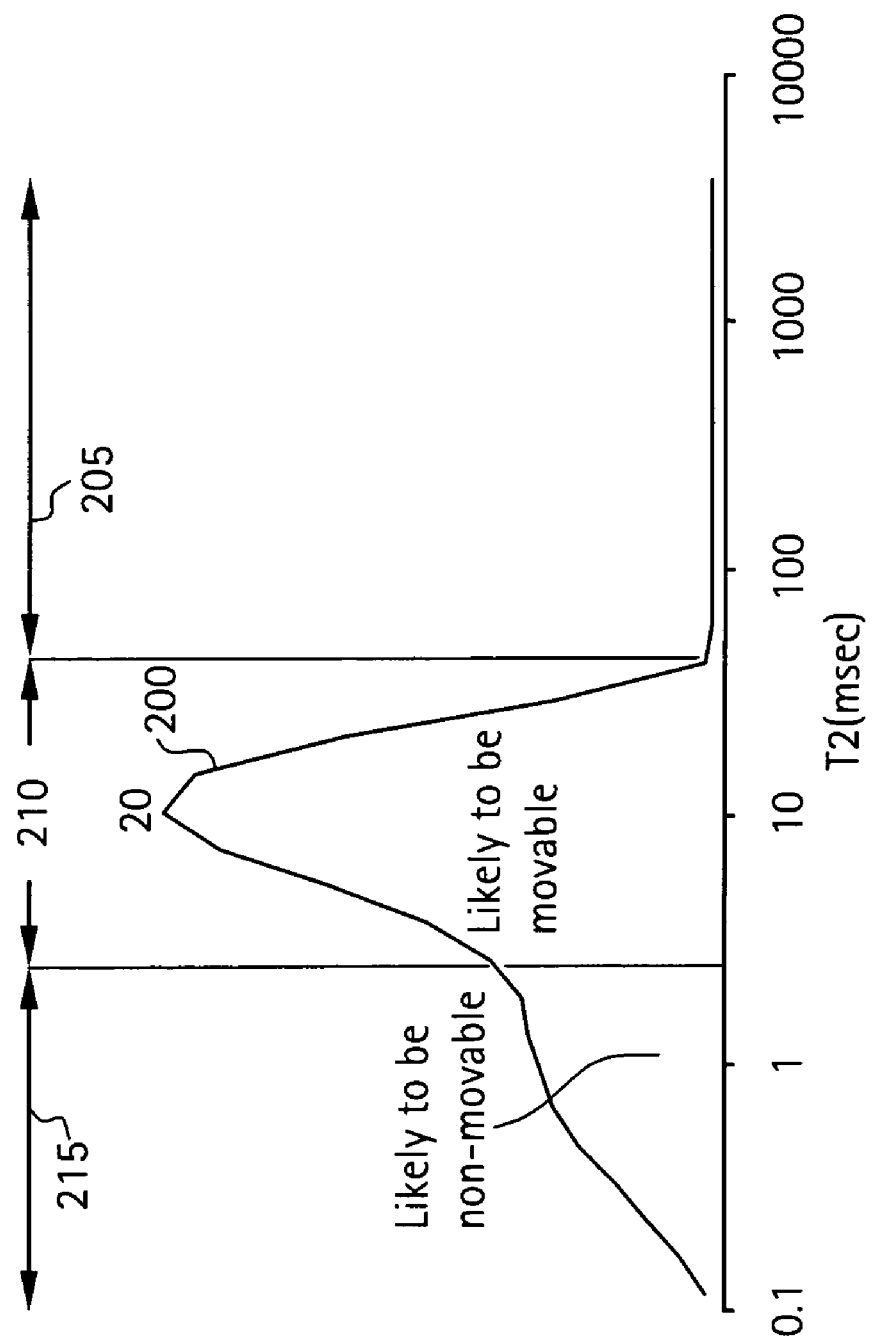
FIG. 2 illustrates a crude oil $T_2$ distribution in accordance with an embodiment of the invention.

A typical crude oil $T_2$ distribution sample 200 is shown in FIG. 2. The less-viscous components are represented by the longer relaxation time portion of the $T_2$ spectra, designated by reference numeral 205. The short relaxation components are more representative of extra viscous and macromolecular hydrocarbons including asphaltene, designated by reference numerals 210, 215. The extra viscous oil and asphaltene are the crude oil components that are less-likely to be recoverable and may even damage reservoir formations by clogging (asphaltene), designated by reference numeral 215. An in-situ method that can distinguish less-viscous, flowable (that is, movable and recoverable), component of heavy oil (reference numeral 210) from the extra viscous component or asphaltene (reference numeral 215) is of economical importance.

In an embodiment, the data processing method utilizes information from a non-NMR log to improve the parameter estimates for formation characteristics and fluid typing from NMR data. In particular, the use of the non-NMR data can overcome the ambiguities of NMR response to heavy oil and bound fluids.

Typical NMR data acquisition methods suitable for heavy oil well characterization include single or plural echo trains that may be acquired with the same or different relaxation time parameters. In general, multiple GTE (gradient multiplied by interecho time) and multiple TW (wait time) are typically used in order to exploit the diffusion contrast and $T_1/T_{2int}$ contrast of the saturation fluids in porous rocks. The intrinsic $T_2$, defined as $$\frac{1}{T_{2int}} = \frac{1}{T_{2bulk}} + \rho \frac{S}{V} \equiv \frac{1}{T_{2bulk}} + \frac{1}{T_{2surf}}, \qquad \text{Equa.-1}$$

is expected to be very close to $T_1$ (longitudinal relaxation time) for most typical fluids in porous media, but may be only a fraction of $T_1$ for heavy oils at low reservoir temperatures and low field experiments, as is expected for fluids under a slow-motion (or rigid-lattice) regime.

As disclosed herein, the following terminology will be employed:

D Diffusivity of fluid.

G Magnetic field gradient. Generally, but not necessarily, G is the NMR tool's field gradient (referred to as being intrinsic). For typical well logging tools, such as MREX$^{SM}$ tool available from Baker Hughes Incorporated, G is frequency dependent. However, a frequency dependent G is not a requirement. In an embodiment, the NMR logging tool has a magnetic field gradient G of about 20 or 40 Gauss/cm.

$T_1$ Longitudinal relaxation time.

$T_2$ Transverse relaxation time.

$T_{2app}$ Apparent $T_2$, where $1/T_{2,app}=1/T_{2,int}+1/T_{2,diff}$.

$T_{2bulk}$ Bulk $T_2$, which is the $T_2$ relaxation time measured in the bulk state. For non-wetting fluids, $1/T_{2bulk} \approx 1/T_{2,int}$.

$T_{2diff}$ Additional $T_2$ decay due to diffusion in a gradient field, where $1/T_{2diff}=(\gamma \cdot G \cdot TE)^2 D/12$.

$T_{2int}$ Intrinsic $T_2$, $1/T_{2,int}=1/T_{2bulk}+1/T_{2surf}$.

$T_{2surf}$ Surface $T_2$, which is the surface contribution of the $T_2$ relaxation time.

TE Interecho time, which is the time between two adjacent echoes. In an embodiment, the NMR logging tool has an echo time spacing TE of about 1 millisecond. TE is variable to achieve the desired GTE combination in a data acquisition scheme.

TW Wait time, which is the time between the last RF pulse applied in the previous data acquisition event and the first excitation pulse of the current data acquisition event of the substantially same frequency.

$\gamma$ Gyromagnetic ratio

R ratio $T_1/T_{2app}$.

The diffusion contrast between heavy oil and water is significantly large, often having several orders of magnitude difference. However, the utility of diffusion contrast for heavy oil quantification may be limited, because for heavy oil and bound water the sensitivity of NMR relaxation time is dominated by the bulk relaxation time ($T_{2bulk}$) for heavy oil, and by the surface relaxation time ($T_{2surf}$) for bound water. Both are included in the intrinsic relaxation time ($T_{2int}$).

In order to maximize the diffusion contrast effect for detection and quantification of different fluid types by NMR measurements, the commonly used approach is to increase the experimentally-controlled parameters to maximize the contrasts of G·TE among different echo trains. The variation of G is limited by the hardware design configuration, and the practical upper limit of TE is controlled by the intrinsic relaxation time. If $TE \geq T_2$ for components of the fluid of interest, the signal intensity will be greatly decreased. Therefore, the range of GTE variation is limited.

An embodiment of the method disclosed herein helps to reduce fluid typing uncertainty in the short relaxation time range and to determine movable vs. non-movable components of the heavy oils. In a first embodiment, the heavy oil $T_2$ range is restricted such that the low $T_2$ bin limit, $T_{2min-HO}$, is set to one that can be reasonably separated from bound water or to the lower-bound of the movable oil $T_2$ distribution. For instance, this limit may be set as the upper limit of the CBW, but it may also be set to a different value, which will be described later. Once the heavy oil range has been reduced, any possible heavy oil components below this range is treated as being inclusive to CBW or bound water. For exemplary purposes, this peudo-CBW is referred to as $CBW_1$. From a data processing point of view, this will not increase the data misfit because if a misfit did occur, it would have implied that the diffusion effect is significant enough to separate the two fluids, which is contradictory to what actually occurs. From a fluid typing interpretation point of view, this could be a misinterpretation, but may be corrected as follows.

In an embodiment of the invention, a non-NMR log based CBW (hereafter denoted $CBW_2$), such as that derived from a gamma ray counter for example, is computed. Alternatively, $CBW_2$ may be obtained from other non-NMR data, such as acoustic slowness or velocity measurements, by comparing the porosity difference between neutron and density logs, or any combination thereof.

In another embodiment, the non-NMR based $CBW_2$, may be obtained by using a prediction method, such as neural network, based on various well log data on similar wells or other depth intervals in the same well.

For heavy oil formations, it is expected that $CBW_1 \geq CBW_2$. The difference $$\Delta CBW = CBW_1 - CBW_2 \qquad \text{Equa.-2}$$

is regarded as the heavy oil components that are not directly observed by the inversion process. The difference $\Delta CBW$ is hereafter denoted $V_{x-HO}$, to present the porosity volume corresponding to the most viscous components in the heavy crude oil. Note that $V_{x-HO}$ is the portion of the oil that may be heavy, contains asphaltenes, and is non-movable. On the other hand, if $CBW_1 < CBW_2$ is found, we interpret the NMR based results as $$CBW = CBW_1 \qquad \text{Equa.-3}$$

and $V_{x-HO}=0$.

Figure 3:
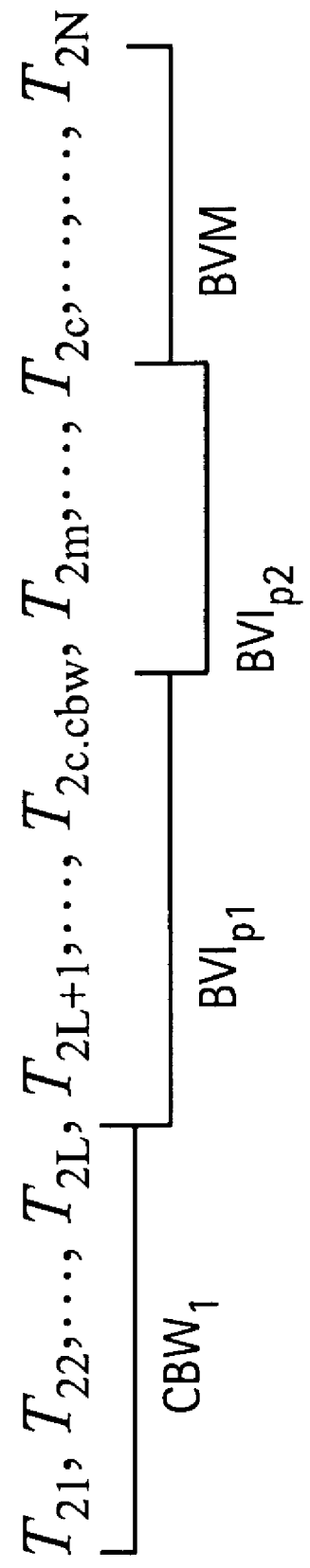
FIG. 3 illustrates inverted bins of a $T_2$ distribution in accordance with an embodiment of the invention.

Even if the $T_{2min-HO}$ is chosen larger than the CBW $T_{2cutoff}$, hereafter denoted as $T_{2c,CBW}$, the above approach is still valid. In this scenario, the directly inverted bins below $T_{2c,CBW}$ includes $CBW_1$ and partial BVI bins, as illustrated in FIG. 3. The BVM bin in FIG. 3 refers to free fluid volume. The scenario illustrated by FIG. 3 is more applicable to cases where clay bound water and capillary bound water $T_2$ partially overlap, or where some rock minerals that cement the sand are radioactive and contribute to the GR reading. In such a case, CBW in Equation-2 is extended to be inclusive partly of the BVI. Accordingly, Equation-2 may still be used to treat the excess "CBW".

By analyzing the NMR data and the non-NMR data such that each of the data provides an apparent clay-bound-water characteristic ($CBW_1$ and $CBW_2$), the difference therebetween will be representative of the volume of heavy oil in the region. The aforementioned analysis of $CBW_1$ versus $CBW_2$ is referred to as extra-heavy oil component estimation by parameter-domain method. In another embodiment of the invention, $CBW_2$ is used as a constraint that builds into the NMR data inversion process.

In the inversion process of NMR data, the model equation may be expressed as:

$$d(t_k, TW_p, TE_q) = \sum_{l=1}^{L} \sum_{j=1}^{N} \sum_{i=1}^{M} m_{i,j} \left[1 - \exp\left(-\frac{TW_p}{R_l \cdot T_{(2int)i}}\right)\right] \quad \text{Equa.-4}$$

$$\exp\left(-\left(\frac{1}{T_{(2int)i}} + \frac{D_j(\gamma \cdot G \cdot TE_q)^2}{12}\right)(t_k)\right)$$

$$t_k = (1, 2, \ldots, K) \cdot TE$$

which may also be expressed in a linear matrix equation format as follows:

$$d = Am, \quad \text{Equa.-5}$$

where d is the experimental data, m is the unknown partial porosity to be determined, and $$A_{ijl} = \left[1 - \exp\left(-\frac{TW_p}{R_l \cdot T_{(2int)i}}\right)\right] \quad \text{Equa.-6}$$

$$\exp\left(-\left(\frac{1}{T_{(2int)i}} + \frac{D_j(\gamma \cdot G \cdot TE_q)^2}{12}\right)(t_k)\right)$$

is the matrix element.

As indicated by Equation-4, the NMR echo signal amplitude decay may be expressed in a multi-exponential model. The general multi-exponential model may be divided into two categories. The first category assumes no knowledge of fluid properties but the broadest possible ranges of the key NMR properties, and the intrinsic relaxation time $T_{(2int)i}$ and diffusivity $D_j$ are always known. This is equivalent to saying that we do not tag any molecule that contributes to NMR signal as a given fluid type, water, oil, or gas, but knowing that the range is set large enough so that the collective contribution of all molecules to the NMR echo amplitude may be expressed by Equation-4. The second category takes into account known reservoir fluid properties and forward models the NMR response for these fluids, thereby enabling the matrix size and the number of unknowns to be reduced. For both categories, the treatment of applying non-NMR CBW constraints is the same.

Data is acquired with different combinations of wait time TW and interecho time TE, which may also have different echo train length K. To obtain the signal intensity $m_{i,j}$ one solves the inversion problem of Equation-4 by solving the matrix equation of Equation-5.

The direct inversion of Equation-6 is ill-conditioned, thus the following regularization term is used:

$$\|Am-d\|_2^2 + \alpha\|W_m m\|_2^2 = \min \text{ subject to } m \geq 0. \quad \text{Equa.-7}$$

In the above expression, the condition $m \geq 0$ is known as a positive constraint, which simply means that all molecules cannot contribute to the total echo signal negatively. This is one example of applying a physical constraint.

In Equation-7, the notation "$\| \ \|$" stands for the Euclidean norm of its vector argument (or the maximum singular value of the matrix argument). The first term $\|Am-d\|$ of Equation-7 comes from Equation-5, and represents the least square portion that serves to minimize the misfit by fitting the model matrix m to the data matrix d. The second term $\alpha\|W_m m\|$ of Equation-7 is a regularization term that serves to penalize the solution by fitting the model matrix m to the data matrix d to a minimum "min" level that is higher than the model and data alone, thereby making the solution more stable and smoother.

The regularization parameter $\alpha$ is estimated from the results of a relatively inexpensive preliminary non-constrained inversion, such that it balances the contributions of the misfit (first) and stabilizer (second) terms. It produces similar $\alpha$ estimates to the well known L-curve or S-curve methods at a lesser cost. Matrix $W_m$ embodies additional information about the desired solution, which is discussed in more detail below. The method of regularization and Least Squares minimization is not limited to a particular algorithm, and employs known techniques.

To single out a useful and stable solution, the stabilizer term in Equation-7 is defined such that $W_m$ is nonsingular. In an exemplary embodiment, it is either the identity matrix or an $n^{th}$ derivative operator, which forces the solution to be small, smooth, or both. However, in NMR logging applications it is often desirable to strive for solutions with a high spectral resolution from noisy data. Such sharp features may be achieved by using focusing stabilizers, where the basic idea is described as follows. After obtaining an initial solution, typically by a smooth stabilizer, very small elements $m_s < \epsilon \cdot \max(m)$ are excluded. Then, a second minimization process is run with $W_m(k,k) = \max(m)/m_k$. A small $m_k$ results in a large weight in the stabilizer of the second step, forcing that particular element to be even smaller. The procedure is repeated until no further elements are excluded, that is, only those elements with significant contribution remain. In applying this process, care should be exercised to avoid over-focusing, where only one or a few elements remain. This may be accomplished by defining different termination criteria, or by applying additional side constraints, which will now be described.

Clay minerals often contain radioactive elements that may be detected by a gamma ray (GR) detector. Clean sand or carbonate formations normally contain much less radioactive materials. Thus, the GR contrast is a useful indicator for identifying shale or clay.

The GR measured at 100% shale and 100% sand depths, along with a porosity log, may be used to construct a clay-bound-water curve, $CBW_{GR}$:

$$CBW_{GR} = \frac{GR - GR_{sd}}{GR_{sh} - GR_{sd}} \cdot \left(\sum_{all} m_{i,j}\right) \quad \text{Equa.-8}$$

Or $$CBW_{GR} = \frac{GR - GR_{sd}}{GR_{sh} - GR_{sd}} \cdot (\phi_{Total} \text{ of a user defined zone})$$

As is known to one skilled in the art, other CBW models may be constructed based on GR.

While $CBW_{GR}$ is used herein to denote a clay-bound-water characteristic based on non-NMR data arising from a gamma ray detector, it will be appreciated, as discussed previously, that other non-NMR data gathering devices may be employed for purposes disclosed herein. Accordingly, the term $CBW_{GR}$ is intended to encompass clay-bound-water characteristics arising from all applicable non-NMR data gathering devices, and not just gamma ray detectors.

For example, embodiments of the invention may use other logging measurements, such as SP (spontaneous potential), acoustic velocity or slowness measurements and density & neutron measurements to construct a CBW curve similar to that with GR. Alternatively, a combination of the foregoing measurements may be used, which may improve the robustness of the non-NMR CBW estimates. Measurement devices other than GR detectors may be useful for improving the overall robustness of the non-NMR CBW indicator as well as providing a robust CBW indicator when testing regions of interest that contain minerals which tend to reduce or negate the effectiveness of a GR detector.

As GR is an indication of radioactive minerals that clay usually possess, it may vary over the depths if the clay composition changes. Thus, one must allow tolerance on $cbw_{GR}$ if using it as a constraint. In an embodiment of the invention, the following tolerances $tor_1$ and $tor_2$ are applied:

$$0 \leq CBW_{GR} - tor_1 \leq \sum_{\substack{T_{2int} < cbw\,cutoff \\ D > water\,diffusivity\,cutoff}} m_{n,m} \leq CBW_{GR} + tor_2 \quad \text{Equa.-9}$$

where:

$CBW_{GR}$ represents a clay-bound-water characteristic arising from the non-NMR data, $tor_1$ represents a first tolerance applied to $CBW_{GR}$, $tor_2$ represents a second tolerance applied to $CBW_{GR}$, $m_{n,m}$ represents the NMR signal intensity, $T_{2int}$ represents intrinsic transverse relaxation time of investigated nuclei in the region, and D represents diffusivity of investigated nuclei in the region.

The two tolerances may be set by a user, or be field specific.

The $CBW_{GR}$ constraint is referred to as a physical constraint.

The application of the $CBW_{GR}$ constraint described above helps to improve the correctness of CBW, but sometimes the heavy oil signal may still be spread across a wide range of diffusivity on a 2D image due to the poor sensitivity of diffusivity in a fast decay range. In order to make the heavy oil identification more easily legible from 2D NMR images, the following numerical constraint may also be optionally applied:

$$\min_m \|\kappa(m)\|_2^2 \quad \text{Equa.-10}$$

where:

$\kappa(m) = \Sigma m_{i,j} w_{i,j}$;

i and j represent indices that may be applied for the entire solution space or a subset of the solution space;

$w_{i,j}$ represents a weighting function rule, such as, for example, $w_{i,j} = 1 - \exp(-d_{i,j}/\max(d_{i,j}))$;

$d_{i,j}$ = min(normalized distance to water line, oil line, and heavy oil line, where the normalized distance is the distance computed in log space of $T_2$ and D);

$T_2$ represents transverse relaxation time of investigated nuclei in the region; and D represents diffusivity of investigated nuclei in the region.

By combining Equation-5 with the two constraints of Equations-9 and 10, the following results:

$$Am = d \quad \text{Equa.-11}$$

subject to $$0 \leq CBW_{GR} - tor_1 \leq \sum_{\substack{T_{2int} < cbw\,cutoff \\ D > water\,diffusivity\,cutoff}} m_{i,j} \leq CBW_{GR} + tor_2$$

and $$\min_m \|\kappa(m)\|_2^2$$

Similar to solving Equation-5 with no constraints, a regularization term is used, such that solving Equation-11 is equivalent to solving the following minimization equation:

$$\|Am - d\|_2^2 + \alpha \|W_m m\|_2^2 + \|\kappa(m)\|_2^2 = \min \quad \text{Equa.-12}$$

subject to $$m \geq 0.$$

and $$0 \leq CBW_{GR} - tor_1 \leq \sum_{\substack{T_{2int} < CBW\,cutoff \\ D > water\,diffusivity\,cutoff}} m_{i,j} \leq CBW_{GR} + tor_2$$

By introducing two new variables, u and v, we convert the $CBW_{GR}$ inequality constraint to the following constraints:

$$CBW \sum_{\substack{T_{2int} < cbw\,cutoff \\ D > water\,diffusivity\,cutoff}} m_{i,j} + u = CBW_{GR} + tor_2 \quad \text{Equa.-13}$$

$$\sum_{\substack{T_{2int} < CBW\,cutoff \\ D > water\,diffusivity\,cutoff}} m_{i,j} - v = CBW_{GR} - tor_1$$

subject to $$u \geq 0, v \geq 0$$

Equation-13 may be combined with Am=d of Equation-S to obtain:

$$A_1 m_1 = d_1 \quad \text{Equa.-14}$$

where $$d_1 = \begin{pmatrix} d \\ CBW_{GR} + tor_1 \\ CBW_{GR} - tor_2 \end{pmatrix}$$

$$m_1 = \begin{pmatrix} m \\ u \\ v \end{pmatrix}$$

$$A_1 = \begin{pmatrix} A & 0 & 0 \\ B & 1 & 0 \\ B & 0 & -1 \end{pmatrix}$$

where B is a vector corresponding to the GR constraint.

In a more compact form, Equation-12 may be reduced to the following:

$$\|A_1 m_1 - d_1\|_2^2 + \alpha \|W_m m\|_2^2 + \|\kappa(m)\|_2^2 = \min \text{ subject to } m,u,v \geq 0 \qquad \text{Equa.-15}$$

In general, each constraint of Equations-9 and 10 may be applied independent of the other.

As can be seen from Equations-14 and 15, the solution equation, the first solution constraint, and the second solution constraint, are combinable such that the solution equation may be solved using embedded solution constraints.

In view of the foregoing, and with reference now to FIG. 4, a method 300 for obtaining a parameter of interest (such as the movable portion of heavy oil components) relating to a subterranean region investigated by a NMR tool and a non-NMR tool, may be applied according to the following: acquiring (305) NMR data arising from the NMR tool, and (310) non-NMR data arising from the non-NMR tool (for example, the non-NMR data from a gamma ray detector is used to construct a clay-bound-water (CBW) characteristic); utilizing (315) a solution equation (such as Equation-4, 5, 7, 11, 12, 14 or 15) for solving for the NMR signal intensity $m_{ij}$ where the solution equation is functionally related to the NMR data (d); utilizing (320) a solution constraint (such as Equation-9 or 10) that is based at least partially on the non-NMR data $CBW_{GR}$; and, solving (325) the solution equation for the signal intensity subject to the solution constraint. As a result, the solution provides information relating to the movable portion of heavy oil components.

In an embodiment, the solution equation includes a matrix element A that defines NMR echo signal amplitude decay in relation to the NMR data, and the solving of the solution equation includes inversion of the matrix element. The solving of the solution equation may also include applying a regularized non-negative least square formulation for stabilizing and smoothing the signal intensity solution.

In an embodiment, the solution constraint includes tolerances $tor_1$ and $tor_2$ on the CBW characteristic, a numerical constraint that is functionally related to the signal intensity, or both.

Once the volume of heavy oil in the region has been determined, the non-movable heavy oil portion of the volume of heavy oil in the region may be defined to be that portion having a transverse relaxation time $T_2$ equal to or less than a defined value, as illustrated in FIG. 1.

An embodiment of the invention may be embodied in the form of computer-implemented processes and apparatuses for practicing those processes. The present invention may also be embodied in the form of a computer program product 330 having computer program code containing instructions embodied in tangible media, such as floppy diskettes, CD-ROMs, hard drives, USB (universal serial bus) drives, RAM (random access memory), ROM (read only memory), EPROM (erasable programmable read only memory), or any other computer readable storage medium, wherein, when the computer program code is loaded into and executed by a computer 335, the computer becomes an apparatus for practicing the invention. The present invention may also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein when the computer program code is loaded into and executed by a computer, the computer becomes an apparatus for practicing the invention. When implemented on a general-purpose microprocessor, the computer program code segments configure the microprocessor to create specific logic circuits. A technical effect of the executable instructions is to distinguish movable and non-movable portions of heavy oil components from wireline logging.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A method for obtaining a parameter of interest relating to a region investigated by a nuclear magnetic resonance (NMR) tool and a non-NMR tool, the method comprising:
   acquiring data arising from the NMR tool;
   acquiring data arising from the non-NMR tool;
   utilizing a solution equation for NMR signal intensity, the solution equation being functionally related to the NMR data;
   utilizing a solution constraint based at least partially on the non-NMR data; and
   solving the solution equation for the signal intensity subject to the solution constraint;
   wherein the solving provides information relating to the parameter of interest.

2. The method of claim 1, wherein the solution equation comprises a matrix element defining NMR echo signal amplitude decay in relation to the NMR data.

3. The method of claim 2, wherein the solving comprises inversion of the matrix element.

4. The method of claim 3, wherein the solving further comprises applying to the solution equation a regularized non-negative least square formulation for stabilizing and smoothing the signal intensity solution.

5. The method of claim 4, wherein the non-NMR data is used to construct a clay-bound-water (CBW) characteristic.

6. The method of claim 5, wherein the non-NMR data is acquired using a Gamma Ray (GR) detector.

7. The method of claim 5, wherein the solution constraint comprises a tolerance on the CBW characteristic.

8. The method of claim 7, wherein the solution constraint further comprises a second tolerance on the CBW characteristic.

9. The method of claim 8, wherein the first and second tolerance are settable by a user or field specific.

10. The method of claim 5, wherein the solution constraint comprises a numerical constraint functionally related to the signal intensity.

11. The method of claim 8, wherein the solution constraint further comprises a second constraint comprising a numerical constraint functionally related to the signal intensity.

12. The method of claim 11, wherein the solution equation, the first solution constraint, and the second solution constraint, are combinable such that the solving comprises solving the solution equation with embedded solution constraints.

13. The method of claim 2, wherein the solution equation is a matrix equation in accordance with the following:

d=A*m;

where:

d represents the acquired NMR data;

A represents the matrix element; and m represents the NMR signal intensity.

14. The method of claim 8, wherein the solution constraint is in accordance with the following:

$$0 \leq CBW_{GR} - tor_1 \leq \sum_{\substack{T_{2int}<CBW\,cutoff \\ D>\text{water diffusivity cutoff}}} m_{n,m} \leq CBW_{GR} + tor_2$$

where:

$CBW_{GR}$ represents a clay-bound-water characteristic arising from the non-NMR data;

$tor_1$ represents a first tolerance applied to $CBW_{GR}$;

$tor_2$ represents a second tolerance applied to $CBW_{GR}$;

$m_{n,m}$ represents the NMR signal intensity;

$T_{2int}$ represents intrinsic transverse relaxation time of investigated nuclei in the region; and D represents diffusivity of investigated nuclei in the region.

15. The method of claim 10, wherein the numerical constraint is in accordance with the following:

$$\min_m \|\kappa(m)\|_2^2;$$

where:

$\kappa(m) = \Sigma m_{i,j} w_{i,j}$;

i and j represent indices that may be applied for the entire solution space or a subset of the solution space;

$w_{i,j}$ represents a weighting function rule;

$d_{i,j}$=min(normalized distance to water line, oil line, and heavy oil line, where the normalized distance is the distance computed in log space of $T_2$ and D);

$T_2$ represents transverse relaxation time of investigated nuclei in the region; and D represents diffusivity of investigated nuclei in the region.

16. The method of claim 15, wherein:

$w_{i,j}=1-\exp(-d_{i,j}/\max(d_{i,j}))$.

17. The method of claim 1, further comprising:

analyzing the NMR data and the non-NMR data such that each of the data provides an apparent clay-bound-water characteristic, the difference therebetween being representative of a volume of heavy oil in the region.

18. The method of claim 17, further comprising:

defining a non-movable heavy oil portion of the volume of heavy oil in the region to be that portion having a transverse relaxation time $T_2$ equal to or less than a defined value.

19. A computer program product comprising a computer readable medium having computer readable program code on or embodied in the medium, the computer readable program code capable of implementing the method of claim 1.

* * * * *